(12) United States Patent
Fischer et al.

(10) Patent No.: US 10,357,308 B2
(45) Date of Patent: Jul. 23, 2019

(54) HIGH-FREQUENCY SURGICAL APPLIANCE

(71) Applicant: OLYMPUS WINTER & IBE GMBH, Hamburg (DE)

(72) Inventors: Uwe Fischer, Berlin (DE); Tino Kirfe, Berlin (DE); Stefan Schiddel, Potsdam (DE); Lutz Kersten, Berlin (DE); Frank Breitsprecher, Berlin (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 320 days.

(21) Appl. No.: 15/310,230

(22) PCT Filed: May 15, 2015

(86) PCT No.: PCT/EP2015/060738
§ 371 (c)(1),
(2) Date: Nov. 10, 2016

(87) PCT Pub. No.: WO2015/173382
PCT Pub. Date: Nov. 19, 2015

(65) Prior Publication Data
US 2017/0135743 A1    May 18, 2017

(30) Foreign Application Priority Data

May 15, 2014   (DE) .................. 10 2014 209 264

(51) Int. Cl.
*A61B 18/12*  (2006.01)
*A61B 18/00*  (2006.01)

(52) U.S. Cl.
CPC .............. *A61B 18/1233* (2013.01); *A61B 2018/00642* (2013.01); *A61B 2018/00678* (2013.01);
(Continued)

(58) Field of Classification Search
CPC ............ A61B 18/1206; A61B 18/1233; A61B 2018/00892; A61B 2018/00827;
(Continued)

(56) References Cited

U.S. PATENT DOCUMENTS 4,727,874 A   3/1988   Bowers et al.
6,142,992 A   11/2000  Cheng et al.
(Continued)

FOREIGN PATENT DOCUMENTS

JP   2004-505662 A   2/2004
JP   2007-289707 A   11/2007
JP   2008-086776 A   4/2008

OTHER PUBLICATIONS

Aug. 17, 2018 Office Action issued in Japanese Patent Application No. 2017-512435.
(Continued)

*Primary Examiner* — Michael F Peffley
*Assistant Examiner* — Amanda L Zink
(74) *Attorney, Agent, or Firm* — Oliff PLC

(57) ABSTRACT

A high-frequency surgical appliance has a peak value detection and control unit, having a current or voltage sensor designed to detect the current strength or the voltage of a high-frequency alternating current output to the load. The control unit has a root-mean-square value former or is connected thereto, connected to the sensor and forms a root-mean-square value of a high-frequency alternating current detected by the sensor. The control unit deactivates the high-frequency generator when, in the steady state of the HF high-voltage circuit, a quantity of an instantaneous peak value of a signal representing an instantaneous value of the high-frequency alternating current detected during operation by the sensor exceeds a quantity of a value derived from the root-mean-square value of the high-frequency alternating
(Continued)

current detected during operation by the sensor. The sensor continuously detects the instantaneous value of the current or voltage flowing during operation into the HF high-voltage circuit.

13 Claims, 3 Drawing Sheets

(52) U.S. Cl.
CPC ............... *A61B 2018/00708* (2013.01); *A61B 2018/00827* (2013.01); *A61B 2018/00892* (2013.01)

(58) Field of Classification Search
CPC .......... A61B 2018/00708; A61B 2018/00642; A61B 2018/00678
See application file for complete search history.

(56) References Cited

U.S. PATENT DOCUMENTS

| | | |
|---|---|---|
| 2004/0030329 A1 | 2/2004 | Hagg |
| 2007/0173806 A1 | 7/2007 | Orszulak et al. |
| 2007/0250052 A1 | 10/2007 | Wham |
| 2008/0082095 A1 | 4/2008 | Shores et al. |
| 2009/0099561 A1* | 4/2009 | McGreevy ......... A61B 18/1442 606/34 |
| 2009/0112204 A1 | 4/2009 | Aronow et al. |
| 2012/0215213 A1 | 8/2012 | Juzkiw et al. |

OTHER PUBLICATIONS

Aug. 20, 2018 Office Action issued in European Patent Application No. 15 726 027.4.

Aug. 18, 2015 International Search Report issued in International Patent Application No. PCT/EP2015/060738.

Aug. 18, 2015 Written Opinion issued in International Patent Application No. PCT/EP2015/060738.

Jan. 28, 2015 Office Action issued in German Patent Application No. 10 2014 209 264.7.

Mar. 14, 2019 Office Action issued in Chinese Patent Application No. 201580025966.3.

* cited by examiner

HIGH-FREQUENCY SURGICAL APPLIANCE

BACKGROUND

The invention relates to a high-frequency surgical appliance having a high-voltage power supply unit and a high-frequency generator, which during operation is supplied by the high-voltage power supply unit and generates a high-frequency alternating current and delivers it to a load, for example a surgical instrument.

Such high-frequency surgical appliances are known from the prior art, for example from U.S. Pat. No. 6,142,992, EP 0 430 929 A2 or WO 2006/050888 A1. Such high-frequency surgical appliances are used in order to supply a corresponding surgical instrument with energy for the purpose of coagulation and cutting tissue. One problem is in this case often represented by current peaks, for example as a result of voltage discharges which may for example lead to arcs. Accordingly, controls which are intended to prevent or end such voltage discharges are described in the aforementioned publications.

There is, however, a need as before for rapid and reliable control.

SUMMARY

To this end, according to the invention, a high-frequency surgical appliance of the type mentioned in the introduction is provided, which has a peak value detection and control unit, which for its part comprises a current or voltage sensor, which is configured in order to detect the current strength or the voltage of a high-frequency alternating current delivered to the load during operation, and comprises or is connected to an rms value forming unit, the rms value forming unit being connected to the current or voltage sensor and configured in order to form an rms value of a high-frequency alternating current detected by the current or voltage sensor. According to the invention, the peak value detection and control unit is configured in order to deactivate the high-frequency generator whenever, in the settled state of the HF high-voltage circuit, a magnitude of an instantaneous peak value of a signal representing an instantaneous value of the high-frequency alternating current detected by the the current or voltage sensor during operation exceeds a magnitude of a value derived from the rms value of the high-frequency alternating current detected by the current or voltage sensor during operation. During operation, the HF high-voltage circuit is formed by the high-frequency generator and the surgical instrument connected thereto. The current or voltage sensor continuously detects the instantaneous value of the current flowing during operation in the HF high-voltage circuit, or of the voltage.

"Exceed" in this case always relates to the magnitudes of the signal representing the respective instantaneous value and of the value derived from the rms value.

The signal representing an instantaneous value of the high-frequency alternating current detected by the current or voltage sensor during operation may be attenuated. The value derived from the rms value of the high-frequency alternating current detected by the current or voltage sensor during operation may then correspond directly to the rms value. What is important is only that the signal representing maximum amplitude of the high-frequency alternating current detected by the current or voltage sensor during operation (i.e. the signal representing the respective instantaneous value) is less in the stable settled state of the HF high-voltage circuit than the value derived from the rms value of the high-frequency alternating current detected by the current or voltage sensor during operation, so that the signal representing the respective instantaneous value exceeds the value derived from the rms value of the high-frequency alternating current detected by the current or voltage sensor during operation only in the event of a sudden rise in the maximum amplitude of the instantaneous value. The invention makes use of the fact that an rms value follows a rise in the maximum amplitude of the associated instantaneous values only with a certain delay.

In order to compare the respective instantaneous value of the current detected by the current or voltage sensor with the value derived from the rms value of this current, the peak value detection and control unit preferably comprises a comparator, which is embodied as a hardware component, i.e. as an analog circuit, and can therefore react very rapidly.

The invention includes the discovery that the rms value of the current increases more slowly than the respective instantaneous value even in the event of current peaks, such as occur for example during voltage discharges (arcs). Correspondingly, a value derived from the rms value also increases relatively slowly. If the value derived from the rms value is for example the respective rms value plus a fixed additional value, so that the deactivation of the high-frequency generator takes place whenever the instantaneous value of the high-frequency alternating current exceeds the rms value plus the fixed additional value, small increases in the instantaneous value lead not to the deactivation of the high-frequency generator but rather to a slow increase in the rms value as well. The comparison value which is used for the detection of current peaks is therefore likewise a sliding comparison value and not a fixed value.

Preferably, the value derived from the rms value of the alternating current detected by the current or voltage sensor is the rms value plus a fixed magnitude (the additional value). This fixed magnitude (or additional value) is selected in such a way that intentional increases in the instantaneous value of the current, for example an intentional power increase, still do not lead to the peak value detection and control unit deactivating the high-frequency generator.

The value derived from the rms value of the alternating current detected by the current or voltage sensor may also be greater than the rms value by a predetermined factor (additional factor), for example 1.5 or 2. It is also possible to provide different additional values or additional factors for different rms values.

As an alternative, the signal representing the respective instantaneous value of the current or of the voltage may be attenuated or reduced.

Furthermore, it is preferred for the peak value detection and control unit to be activated only with a delay relative to an activation of the high-voltage power supply unit and of the high-frequency generator. This is because, immediately after starting of the high-voltage power supply unit and/or of the high-frequency generator, the instantaneous value of the current detected by the current or voltage sensor increases relatively strongly from period to period until a settled state is reached. Directly after switching on of the high-voltage power supply unit or of the high-frequency generator, the rms value is initially zero and thereupon at first increases slowly, so that the instantaneous value regularly lies significantly above the rms value and possibly even above the rms value plus the fixed magnitude, i.e. even above the value derived from the rms value. So that deactivation of the high-frequency generator by the peak value detection and control unit does not take place in this case, the latter is activated only with a certain delay. To this end, a control unit is preferably provided, which ensures this delay and provides an activation signal for the peak value detection and control unit only after a certain time delay.

As an alternative, provision may also be made for the signal representing the respective instantaneous value of the current or of the voltage to be compared with a predetermined minimum value, and for a switch-off signal to be generated only if the signal representing the respective instantaneous value of the current or of the voltage has exceeded not only the value derived from the rms value but also the predetermined minimum value.

Preferably, the peak value detection and control unit is connected to the high-frequency generator in such a way that the peak value detection and control unit deactivates the high-frequency generator by preventing the delivery of drive pulses to the high-frequency generator. Typically, a high-frequency generator is periodically supplied with drive pulses having a frequency which corresponds to the resonant frequency of the high-frequency generator, in order to sustain the resonant oscillation. If the delivery of these drive pulses ceases, the high-frequency generator temporarily no longer delivers a high-frequency alternating current. The peak value detection and control unit is preferably embodied as a hardware component, which can directly process analog input signals coming from the current or voltage sensor. Preferably, the peak value detection and control unit contains a comparator for analog comparison of the instantaneous value of the alternating current detected by the current or voltage sensor and the rms value of the alternating current. In this way, the peak value detection and control unit can generate a switch-off signal, which deactivates the high-frequency generator, in the shortest possible time when the instantaneous value of the current exceeds the value derived from the rms value.

Preferably, the peak value detection and control unit furthermore has an input for an activation signal, with which the peak value detection and control unit can be activated or deactivated. In this way, for example, activation of the peak value detection and control unit with a time delay is possible. It is in this way also possible to avoid erroneous deactivation being able to take place in particular operating modes, namely when current or voltage peaks that are intentional occur because of a corresponding operating mode. It is therefore advantageous for the peak value detection and control unit to be deactivated in the event of selection of such operating modes. This may, for example, be carried out automatically by a software-controlled central control unit whenever an operating mode that entails intentional current or voltage peaks is selected or switched on.

According to another preferred alternative embodiment, the peak value detection and control unit has a further input to which a signal is applied that represents the fixed magnitude by which the value derived from the rms value differs from the rms value. This input for a signal representing a fixed magnitude is preferably likewise connected to a further control unit, for example to the control unit which also causes time-delayed activation of the peak value detection and control unit.

This further control unit is preferably a software-controlled central control unit which is programmable and undertakes less time-critical control tasks.

In a preferred alternative embodiment, the high-frequency surgical appliance additionally comprises a voltage control unit which is connected on the output side to the high-voltage power supply unit and which is connected on the input side at least indirectly to the peak value detection and control unit. This voltage control unit is configured in order to output a voltage control signal for the high-voltage power supply unit. On the input side, the voltage control unit is connected at least indirectly to the output of the peak value detection and control unit, so as to be able to receive the output signal at the peak value detection and control unit. If the peak value detection and control unit outputs a control signal deactivating the high-frequency generator, this control signal can simultaneously cause the voltage control unit to generate a voltage control signal that causes a reduction of the output voltage delivered by the high-voltage power supply unit. In this way, for example, it is possible to avoid an immediate new voltage discharge when the high-frequency generator is activated again.

The voltage control unit is preferably produced as an analog circuit having at least one further input, which is connected to a control unit that is software-controlled, i.e. for example to a programmable central control unit of the high-frequency surgical appliance. In this way, the advantages of programmable control, for example for different surgical applications, can be combined with one another with the advantages of an analog circuit—for example rapid reaction in the event of an arc.

The current rms value forming unit contains at least one unit for forming a root mean square value (rms).

BRIEF DESCRIPTION OF THE DRAWINGS

The invention will now be explained in more detail with the aid of an exemplary embodiment with reference to the figures. In the figures:

FIG. 3: shows a second diagram to explain the functionality of the high-frequency surgical appliance after switching on.

DETAILED DESCRIPTION

Figure 1:
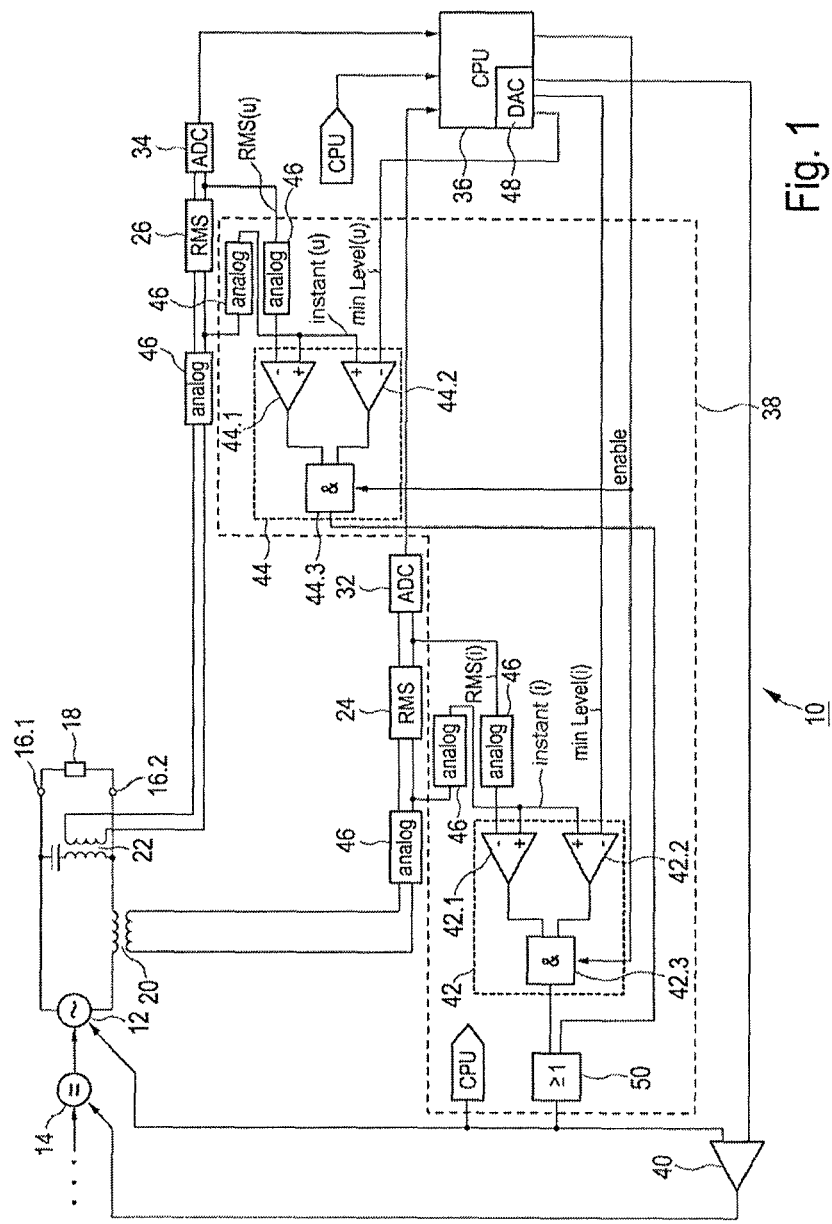
FIG. 1: shows a schematic block diagram of a high-frequency surgical appliance according to the invention.

The high-frequency surgical appliance 10 depicted in FIG. 1 contains a high-frequency generator 12, which is supplied by a high-voltage power supply unit 14. High-frequency alternating current generated by the high-frequency generator 12 can be delivered to a connected instrument 18 via two terminals 16.1 and 16.2. The instrument 18 represents a load for the HF high-voltage circuit supplied by the high-frequency generator 12. The HF high-voltage circuit includes the high-frequency generator 12 and the instrument 18.

A current sensor 20 is provided in order to detect the current flowing in the HF high-voltage circuit during operation, and a voltage sensor 22 is provided in order to detect the voltage respectively prevailing. The values detected by the current sensor 20 and the voltage sensor 22 are each sent to an RMS unit 24 and 26, respectively, via analog matching circuits 46. The RMS unit 24 forms an rms value of the current, and the RMS unit 26 forms an rms value of the voltage. These rms values are respectively sent to an analog/digital converter 32 and 34. The current and voltage rms values digitized by the respective digital converter 32 and 34 are sent to a software-controlled central control unit 36.

Besides the software-controlled central control unit 36, two control units embodied in the form of hardware components and each containing at least one comparator are furthermore provided, namely a peak value detection and control unit 38 and a voltage control unit 40.

The peak value detection and control unit 38 is connected on the output side to the high-frequency generator 12, and can output a switch-off signal for the high-frequency generator 12.

In the exemplary embodiment represented, the peak value detection and control unit 38 comprises a peak current detection unit 42 and a peak voltage detection unit 44. In contrast thereto, it is also possible for the peak value detection and control unit 38 to comprise only either a peak current detection unit or a peak voltage detection unit.

The peak current detection unit 42 and the peak voltage detection unit 44 are in principle (i.e. apart from circuit details which are not represented in the figure) constructed identically. Both the peak current detection unit 42 and the peak voltage detection unit 44 respectively comprise a first comparator 42.1 and 44.1, to which the rms value of the current or voltage is respectively supplied via a first input (in this case, the respective inverting input). To this end, the first (in the exemplary case inverting) input of the first comparator 42.1 or 44.1 is connected to an output of the RMS unit 24 or of the RMS unit 26, respectively, in such a way that a signal representing the respective rms value of the current or of the voltage in the HF high-voltage circuit is applied to the first input of the first comparator 42.1 or 44.1. A respective second (in the exemplary embodiment noninverting) input of the respective first comparator 42.1 or 44.1 is respectively connected to the current sensor 20 or the voltage sensor 22 in such a way that a signal representing the respective instantaneous value of the current or of the voltage is applied to the second input. In this way, a signal representing the instantaneous value of the current or of the voltage is in each case supplied to the respective second input of the respective first comparator 42.1 or 44.1, so that the respective first comparator 42.1 or 44.1 compares a respective instantaneous value of the current or of the voltage with a value, derived from the corresponding rms value, of the current or of the voltage. The two inputs are respectively preceded by analog matching circuits 46, which if need be ensure current or voltage conversion or impedance matching.

By means of the analog matching circuits, the respective rms value can be increased in relation to the instantaneous values on which it is based, and thus become a value derived from the high-frequency alternating current detected by the current or voltage sensor during operation.

Such a relative increase in the respective rms value relative to the instantaneous values on which it is based may also be carried out by attenuation (i.e. reduction of the amplitude) of the instantaneous values by means of corresponding matching circuits 46.

The output of the respective first comparator 42.1 or 44.1 delivers the voltage value which corresponds to a logical 1 when the instantaneous value of the current or of the voltage exceeds the value derived from the corresponding rms value.

The peak current detection unit 42 and the peak voltage detection unit 44 furthermore also respectively comprise a second comparator 42.2 and 44.2, of which the respective noninverting input is connected, precisely like the corresponding input of the respective first comparator 42.1 or 44.1, to the current sensor 20 or the voltage sensor 22, respectively in such a way that a signal representing a respective instantaneous value of the current or of the voltage is likewise applied to the noninverting input of the respective second comparator 42.2 or 44.2. In this way, a signal representing the instantaneous value of the current or of the voltage is also respectively supplied to the respective noninverting input of the respective second comparator 42.2 or 44.2 during operation.

The respective inverting input of the respective second comparator 42.2 or 44.2 is connected via a digital/analog converter 48 two the software-controlled central control unit 36. The software-controlled central control unit 36 can in this way specify a minimum value for the instantaneous value of the current or of the voltage, which must be exceeded so that the respective second comparator 42.2 or 44.2 delivers an output signal corresponding to a logical 1.

The two output signals of the respective first comparator 42.1 or 44.1 and of the respective second comparator 42.2 or 44.2 are respectively supplied to an AND element 42.3 or 44.3. The respective AND element 42.3 or 44.3 delivers signal representing a logical 1 at its output only when both comparators of the peak current detection unit 42 or of the peak voltage detection unit 44 respectively deliver output signal representing a logical 1. This is the case whenever the respective instantaneous value of the current or the voltage exceeds both a respective minimum value of the current or voltage, specified by the software-controlled central control unit 36, and the respective rms value of the current or of the voltage. As a result, this means that both the peak current detection unit 42 and the peak voltage detection unit 44 deliver an output signal corresponding to a logical 1 only when the HF high-voltage circuit including the high-frequency generator 12 and the instrument 18 has settled to such an extent that the instantaneous value of the current or the voltage in each case exceed the minimum value specified by the software-controlled central control unit 36.

The two AND elements 42.3 and 44.3 respectively have an activation input, by which the AND elements 42.3 and 44.3 can be activated by the software-controlled central control unit 36. The respective activation input of the AND elements 42.3 and 44.3 is therefore likewise connected to the software-controlled central control unit 36 and configured in order to receive an enable signal therefrom so as to be activated on account thereof. If such an enable signal is absent, the peak value detection and control unit 38 is not activated.

The output signals of the peak current detection unit 42 and of the peak voltage detection unit 44 (i.e. signals respectively representing a logical "1" or logical "0") are sent to an OR element 50 of the peak value detection and control unit 38, so that the peak value detection and control unit 38 always delivers an output signal representing a logical 1 when the two AND elements 42.3 and 44.3 are respectively activated by a corresponding enable signal of the software-controlled central control unit 36 and furthermore the instantaneous value of the current or the instantaneous value of the voltage exceeds both the respective minimum value predefined respectively by the software-controlled central control unit 36 and the respective rms value of current or the voltage. The output signal of the peak value detection and control unit 38 is sent on the one hand to the software-controlled central control unit 36 and on the other hand to the high-frequency generator 12 as a switch-off signal. This means that the high-frequency generator 12 no longer receives drive pulses when the output of the peak value detection and control unit 38 delivers a signal representing a logical 1. In this way, the high-frequency generator 12 can be deactivated in the shortest time.

Figure 2:
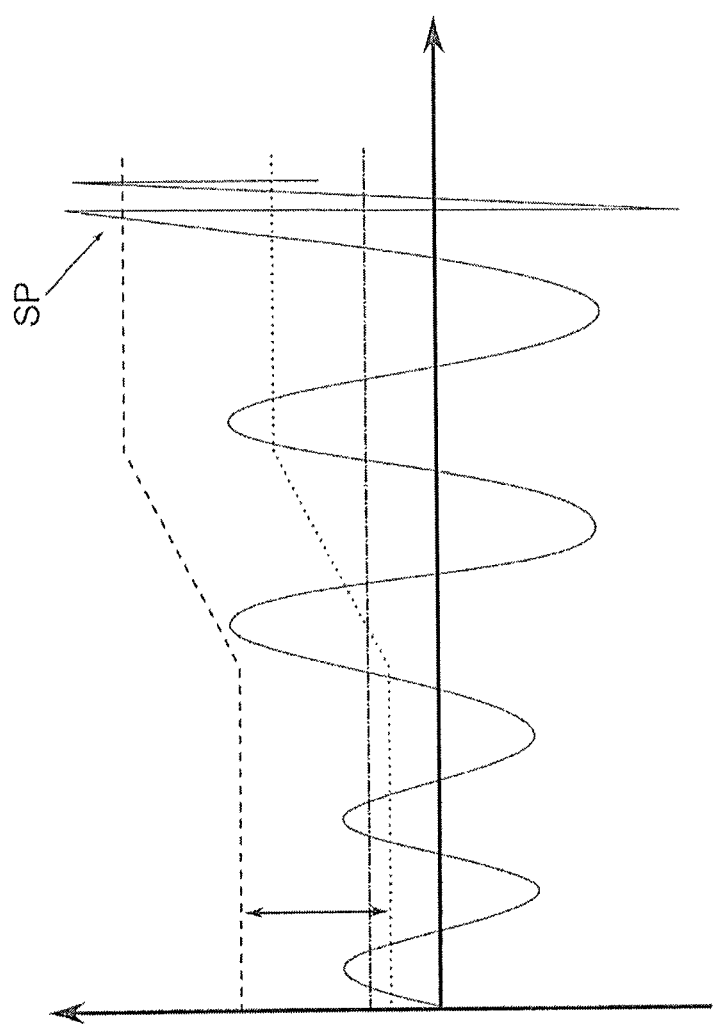
FIG. 2: shows a first diagram to explain the functionality of the high-frequency surgical appliance in the event of the detection of a spark discharge.

As illustrated in more detail in FIG. 2, the peak value detection and control unit 38 therefore generates a switch-off signal, and outputs this to the high-frequency generator 12, whenever an instantaneous value of the exceeds the rms value of the current and the respective minimum value specified by the software-controlled central control unit 36. The switch-off signal causes delivery of drive pulses to the high-frequency generator 12 to cease, so that as a result the latter no longer delivers a high-frequency alternating current.

FIG. 2 shows in a solid line the instantaneous value of the (alternating) current or of the (alternating) voltage in the HF high-voltage circuit. A signal representing this instantaneous value is applied to the noninverting inputs of the comparators 42.1, 44.1, 42.2 and 44.2. A dot-and-dash line represents the minimum value specified by the software-controlled central control unit 36, which is applied to the respective inverting input of the corresponding second comparator 42.4 or 44.2. A dotted line represents the rms value of the current or voltage in the HF high-voltage circuit. A dashed line indicates the rms value, increased by a fixed magnitude, of the current or of the voltage in the HF high-voltage circuit, and therefore a value derived high-frequency alternating current detected by the current or voltage sensor during operation, as is supplied to the inverting input of the corresponding first comparator 42.1 or 44.1.

Since the value derived from the rms value is selected in such a way that the instantaneous value does not yet exceed the value derived from the rms value in the event of an intentional variation of the delivered power, a power increase is possible as shown in FIG. 2. Only when a sudden and large increase occurs, as for example in the case of a spark discharge, does the instantaneous value exceed the value derived from the rms value and the peak value detection and control unit 38 respond; see FIG. 2 at "SP".

Since the comparison of the respective instantaneous value of the current with the rms value of the current is carried out by means of a comparator of the peak value detection and control unit 38, the switch-off signal is generated very rapidly if appropriate and the drive pulses for the high-frequency generator 12 can be switched off within a few μs, for example within 5 μs, after the occurrence of a current peak, for example as a result of a spark discharge.

The switch-off signal is supplied not only to the high-frequency generator 12 but furthermore to the voltage control unit 40, which is likewise configured as a hardware controller. The voltage control unit 40 generates a control signal for the high-voltage power supply unit 14 as an output signal. Input values of the voltage control unit 40 are, besides the switch-off signal of the peak value detection and control unit 38, also a reference value generated by the central control unit 36. Since the central control unit is software-controlled, the reference value generated by the central control unit 36 is converted into an analog reference value respectively by means of the digital/analog converter 48.

Because the switch-off signal of the peak value detection and control unit 38 is also supplied to the voltage control unit 40, in the event of a spark discharge the voltage control unit 40 can generate a control signal which leads to a reduction of the output voltage of the high-voltage power supply unit 14. Since this is carried out in a purely analog fashion, the voltage regulation in the event of a spark discharge likewise takes place very rapidly. In other regards, the voltage regulation is carried out by means of the software-controlled central control unit 36 and the current or voltage values generated by it.

The voltage control unit 40 may be configured as an AND element or as an OR element, or alternatively as a monoflop.

Figure 3:
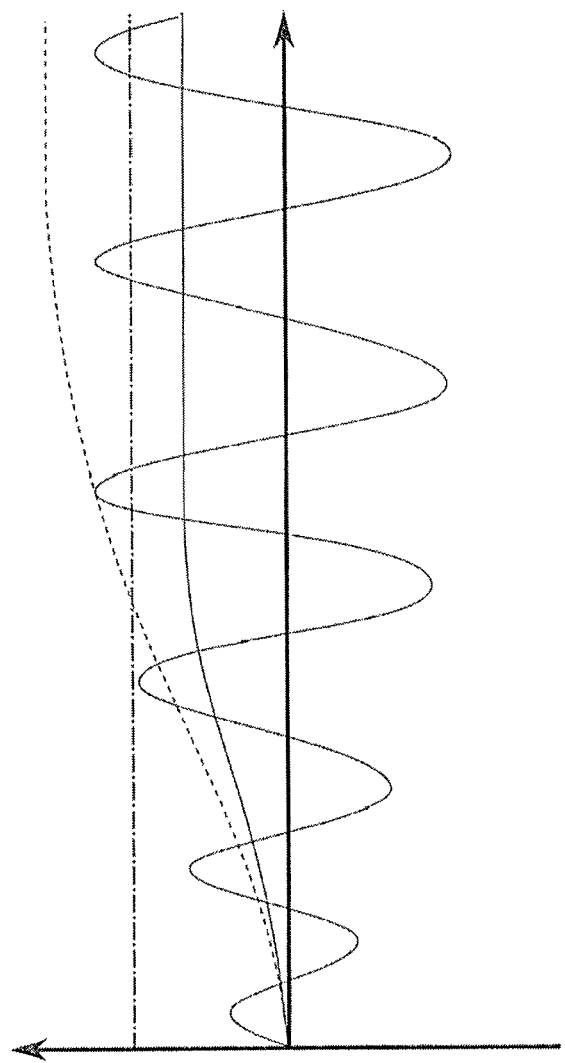

FIG. 3 shows that the peak value detection and control unit 38 responds whenever the respective instantaneous value exceeds both the value derived from the rms value (dashed line) and the predetermined minimum value (dot-and-dash line). This prevents the peak value detection and control unit 38 from already responding when the instantaneous value exceeds the value derived from the rms value immediately after the high-frequency generator 12 is switched on, only because the HF high-voltage circuit is only just settling and the rms value only follows slowly the maximum amplitude of the instantaneous value, which increases rapidly during settling.

The invention claimed is:

1. A high-frequency surgical appliance comprising a high-voltage power supply unit and a high-frequency generator, the high-frequency surgical appliance: (1) being supplied with energy by the high-voltage power supply unit; (2) during operation, generating a high-frequency alternating current and delivering the high-frequency alternating current to a load; and (3) including a peak value detection and control unit that includes or is connected to:
   a current or voltage is sensor configured to detect current strength or voltage of the high-frequency alternating current delivered to the load during operation; and
   an rms value forming unit connected to the current or voltage sensor and configured to form an rms value of the high-frequency alternating current detected by the current or voltage sensor,
   wherein:
   the peak value detection and control unit is configured to deactivate the high-frequency generator when a first magnitude of a signal representing an instantaneous value of the high-frequency alternating current detected by the current or voltage sensor during operation exceeds a second magnitude of a value derived from the rms value of the high-frequency alternating current detected by the current or voltage sensor during operation; and
   the value derived from the rms value of the high-frequency alternating current detected by the current or voltage sensor during operation corresponds to an absolute value, increased by a predetermined extent based on the second magnitude, of the rms value or corresponds directly to the rms value.

2. The high-frequency surgical appliance as claimed in claim 1, wherein the value derived from the rms value of the high-frequency alternating current detected by the current or voltage sensor during operation corresponds to the absolute value, increased by a factor, of the rms value or to the absolute value of the rms value plus a predetermined magnitude.

3. The high-frequency surgical appliance as claimed in claim 1, wherein the signal representing an instantaneous value of the high-frequency alternating current detected by the current or voltage sensor during operation is attenuated or is reduced in respect of its magnitude.

4. The high-frequency surgical appliance as claimed in claim 1, wherein the high-frequency generator and the peak value detection and control unit are connected to one another in such a way that the peak value detection and control unit deactivates the high-frequency generator by preventing the delivery of drive pulses to the high-frequency generator.

5. The high-frequency surgical appliance as claimed in claim 1, wherein the peak value detection and control unit is produced as an analog circuit, which processes analog signals coming from the current or voltage sensor in an analog fashion and to this end contains a comparator.

6. The high-frequency surgical appliance as claimed in claim 1, wherein the peak value detection and control unit is configured, and connected to the high-frequency generator, in such a way that the peak value detection and control unit deactivates the high-frequency generator by preventing the delivery of drive pulses to the high-frequency generator.

7. The high-frequency surgical appliance as claimed in claim 1, wherein the peak value detection and control unit has an input for an activation signal.

8. The high-frequency surgical appliance as claimed in claim 1, having a control unit configured to activate the peak value detection and control unit with a time delay relative to an activation of the high-voltage power supply unit or of the high-frequency generator.

9. The high-frequency surgical appliance as claimed in claim 1, wherein the peak value detection and control unit has an input to which a signal is applied that represents a fixed magnitude or a factor by which the value derived from an absolute value of the rms value differs from the absolute value of the rms value.

10. The high-frequency surgical appliance as claimed in claim 9, wherein the input for the signal representing the fixed magnitude or the factor is connected to a control unit which is software-controlled.

11. The high-frequency surgical appliance as claimed in claim 1, wherein:

a voltage control unit is connected on an output side to the high-voltage power supply unit and is connected on an input side at least indirectly to the peak value detection and control unit, the voltage control unit is configured to generate as an output signal such that, in response to an output signal of the peak value detection and control unit, a voltage control signal is generated, which causes a reduction of the voltage delivered by the high-voltage power supply unit.

12. The high-frequency surgical appliance as claimed in claim 11, wherein the voltage control unit is produced as an analog circuit having at least one further input, which is connected to a control unit that is software-controlled.

13. The high-frequency surgical appliance as claimed in claim 1, wherein the rms value forming unit contains at least one unit for forming a root mean square value (rms).

* * * * *